(12) United States Patent
Young et al.

(10) Patent No.: US 6,794,494 B1
(45) Date of Patent: Sep. 21, 2004

(54) CANCEROUS DISEASE MODIFYING ANTIBODIES

(75) Inventors: David S. F. Young, Toronto (CA); Susan E. Hahn, Toronto (CA)

(73) Assignee: Arius Research, Inc., Ontario (CA)

( * ) Notice: Subject to any disclaimer, the term of this patent is extended or adjusted under 35 U.S.C. 154(b) by 0 days.

(21) Appl. No.: 10/413,755

(22) Filed: Apr. 14, 2003

(51) Int. Cl.[7] .................... C07K 16/00; A61K 39/395; C12P 21/04; C12N 15/02

(52) U.S. Cl. ................... 530/388.8; 530/387.3; 530/387.8; 530/388.1; 424/133.1; 424/138.1; 424/141.1; 424/155.1; 435/70.21; 435/449

(58) Field of Search ............ 424/133.1, 138.1, 424/141.1, 181.1, 183.1; 530/387.3, 387.7, 388.1, 809, 387.1; 435/70.21, 449

(56) References Cited

U.S. PATENT DOCUMENTS

| | | |
|---|---|---|
| 4,861,581 A | 8/1989 | Epstein et al. |
| 5,171,665 A | 12/1992 | Hellstrom et al. |
| 5,484,596 A | 1/1996 | Hanna, Jr. et al. |
| 5,693,763 A | 12/1997 | Codington et al. |
| 5,750,102 A | 5/1998 | Eisenbach et al. |
| 5,780,033 A | 7/1998 | Torchilin et al. |
| 5,783,186 A | 7/1998 | Arakawa et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 * | 1/2001 | Young et al. .............. 435/7.23 |

OTHER PUBLICATIONS

Fundamental Immunology 242 (William E. Paul, M.D. ed., 3d ed. 1993).*

* cited by examiner

*Primary Examiner*—Larry H. Helms
*Assistant Examiner*—David Blanchard
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

10 Claims, 1 Drawing Sheet

CANCEROUS DISEASE MODIFYING ANTIBODIES

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays, which utilize the CDMABs of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment can not be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-her 2 antibody in combination with Cis-platin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only one patient having a partial response. In other trials, use of 17-1A produced only one complete response and two minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung cancer, brain cancers, ovarian cancers, pancreatic cancer, prostate cancer, and stomach cancer. There has been some limited success in the use of anti-GD3 monoclonal antibody for melanoma. Thus, it can be seen that despite successful small animal studies that are a prerequisite for human clinical trials, the antibodies that have been tested have been for the most part ineffective.

PRIOR PATENTS

U.S. Pat. No. 5,750,102 discloses a process wherein cells from a patient's tumor are transfected with MHC genes, which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies, which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies, which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

The instant inventors have previously been awarded U.S. Pat. 6,180,357, entitled "Individualized Patient Specific Anti-Cancer Antibodies" directed to a process for selecting individually customized anti-cancer antibodies, which are useful in treating a cancerous disease.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

Furthermore, it is within the purview of this invention to conjugate standard chemotherapeutic modalities, e.g. radionuclides, with the CDMABs of the instant invention, thereby focusing the use of said chemotherapeutics.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C-1 component of the complement system thereby activating the classical pathway of complement activation, which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative cancer antigen that resides on the tumor cell. The second is the use of antibodies to target growth receptors and interfere with their function or to down regulate that receptor so that effectively its function is lost.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies, which are useful for in a binding assay for diagnosis, prognosis, and monitoring of cancer.

Other objects and advantages of this invention will become apparent from the following description wherein are set forth, by way of illustration and example, certain embodiments of this invention.

EXAMPLE 1

Hybridomas Production—Hybridoma Cell Line 10A304.7

Figure 1:
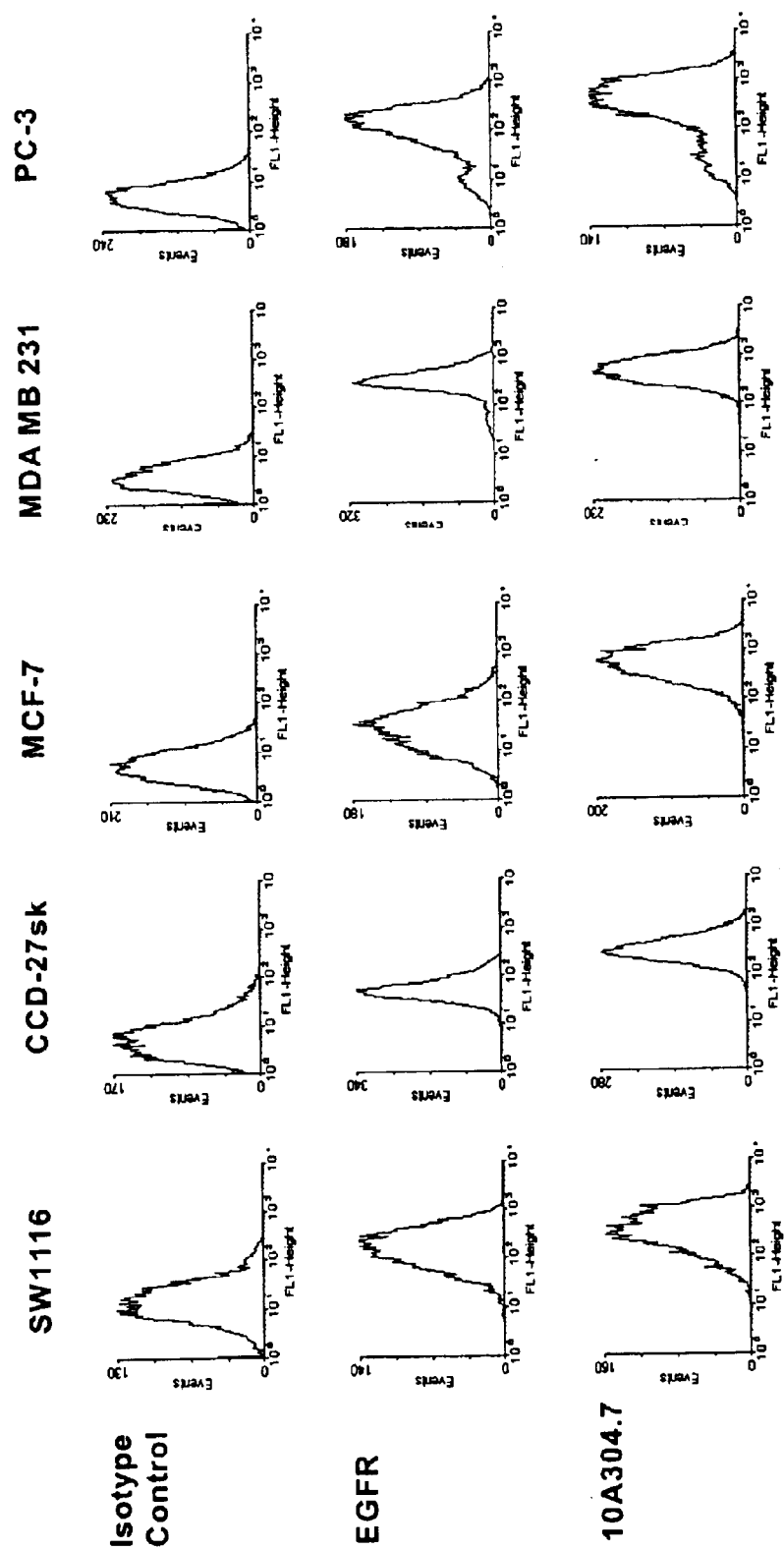
FIG. 1 includes representative FACS histograms of 10A304.7 antibodies, isotype control antibodies, anti-EGFR antibodies directed against several cancer cell lines and non-cancer cells.

The hybridoma cell line 10A304.7 was deposited, in accordance with the Budapest Treaty, with the American Type Culture Collection, 10801 University Blvd., Manassas, Va. 20110-2209 on Nov. 26, 2002, under Accession Number PTA-5065. In accordance with 37 CFR 1.808, the depositors assure that all restrictions imposed on the availability to the public of the deposited materials will be irrevocably removed upon the granting of a patent.

To produce the hybridoma that produces anti-cancer antibody, single cell suspensions of a colon tumor grown in SCID mice from the HT-29 colon cancer cell line were prepared in cold PBS. IMMUNEASY™ (Qiagen, Venlo, Netherlands) adjuvant was prepared for use by gentle vortexing. 100 microliters of IMMUNEASY™ mouse adjuvant were added to 10 million HT-29 cells in the microcentrifuge tube and mixed and left at room temperature for 15 min. Eight to nine weeks old BALB/c mice were immunized by injecting 100 microliters of the antigen-adjuvant containing 2.5 million cells intramuscularly. Freshly prepared antigen-adjuvant was used to boost the immunized mice two weeks after the initial immunization at 2.5 million cells in 250 microliters by an intraperitoneal injection. A spleen was used for fusion two days after the last immunization. The hybridomas were prepared by fusing the isolated spleno-cytes with NSO-1 myeloma partners. The supernatants from the fusions were tested for subcloning of the hybridomas.

To determine whether the antibodies secreted by hybridoma cells are of the IgG or IgM isotype, an ELISA assay was employed. 100 microliters/well of goat anti-mouse IgG +IgM (H+L) at a concentration of 2.4 micrograms/mL in coating buffer (0.1M carbonate/bicarbonate buffer, pH 9.2–9.6) at 4° C. was added to the ELISA plates overnight. The plates were washed thrice in washing buffer (PBS+ 0.05% Tween). 100 microliters/well blocking buffer (5% milk in wash buffer) was added to the plate for 1 hr. at room temperature and then washed thrice in washing buffer. 100 microliters/well of hybridoma supernatant was added and the plate incubated for 1 hr. at room temperature. The plates were washed thrice with washing buffer and 1/5000 dilution of either goat anti-mouse IgG or IgM horseradish peroxidase conjugate (diluted in PBS containing 1% bovine serum albumin), 100 microliters/well, was added. After incubating the plate for 1 hr. at room temperature the plate was washed thrice with washing buffer. 100 microliters/well of TMB solution was incubated for 1–3 minutes at room temperature. The color reaction was terminated by adding 100 microliters/well 2M $H_2SO_4$ and the plate was read at 450 nm with a Perkin-Elmer HTS7000 plate reader. As indicated in Table 1 the 10A304.7 hybridomas secreted primarily antibodies of the IgG isotype.

After one round of limiting dilution hybridona supernatants were tested for antibodies that bound to target cells in a cell ELISA assay. Three colon cancer cell lines were tested: HT-29, SW1116 and SW620. The plated cells were fixed prior to use. The plates were washed thrice with PBS containing $MgCl_2$ and $CaCl_2$ at room temperature. 100 microliters of 2% paraformaldehyde diluted in PBS was added to each well for ten minutes at room temperature and then discarded. The plates were again washed with PBS containing $MgCl_2$ and $CaCl_2$ three times at room temperature. Blocking was done with 100 microliters/well of 5% milk in wash buffer (PBS+0.05% Tween) for 1 hr. at room temperature. The plates were washed thrice with wash buffer and the hybridoma supernatant was added at 100 microliters/ well for 1 hr. at room temperature. The plates were washed three times with wash buffer and 100 microliters/well of 1/5000 dilution of goat anti-mouse IgG or IgM antibody conjugated to horseradish peroxidase (diluted in PBS containing 1% bovine serum albumin) was added. After one hour incubation at room temperature the plates were washed three times with wash buffer and 100 microliter/well of TMB substrate was incubated for. 1–3 minutes at room temperature. The reaction was terminated with 100 microliters/well 2M $H_2SO_4$ and the plate read at 450 nm with a Perkin-Elmer HTS7000 plate reader. The results as tabulated in Table 1 were expressed as the number of folds above background compared to the IgG isotype control (3BD-27). The antibodies from the 10A304.7 hybridoma had 22.8 fold, 13.1 fold, and 23.9 fold greater binding above background in HT-29, SW1116, and SW620 cells, respectively. This indicated that the antibody bound to an antigen that was expressed more so on some cancer cells than others.

In conjunction with testing for antibody binding the cytotoxic effect of the hybridoma supernatants were tested in the same colon cancer cell lines: HT-29, SW11116 and SW620. The Live/Dead cytotoxicity assay was obtained from Molecular Probes (Eu,OR). The assays were performed according to the manufacturer's instructions with the changes outlined below. Cells were plated before the assay at the predetermined appropriate density. After 2 days, 100 microliters of supernatant from the hybridoma microtitre plates were transferred to the cell plates and incubated in a 5% $CO_2$ incubator for 5 days The wells that served as the positive controls were aspirated until empty and 100 microliters of sodium azide and/or cycloheximide was added. 3BD-27 monoclonal antibody was also added as an isotype control since it was known not to bind to HT-29 colon cancer cells. An anti-EGFR antibody (C225) was also used in the assay for comparison. After 5 days of treatment, the plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results were tabulated in Table 1. The 10A304.7 hybridoma produced specific cytotoxicity of 11% in SW1116 cells, which was similar to that obtained with the anti-EGFR antibody C225. The strong binding of 10A304.7 to SW1116 cells indicated that this level of antibody binding was sufficient to mediate cytotoxicity against these cancer cells. Although there was strong binding of the 10A304.7

Biosciences, Oakville, ON), MPC-11 (antigenic specificity unknown, IgG2b, kappa, 20 mg/mL), IgG Buffer (2%)) controls in a cytotoxicity assay (Table 2). Breast cancer (MB-231, MCF-7), colon cancer (Caco-2, DLD-1, Lovo, HT-29, SW1116, SW620), ovarian cancer (OVCAR), pancreatic cancer (BxPC-3), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene,Oreg.). The assays were performed according to the manufacturer's instructions with the changes outlined below. Cells were plated before the assay at the predetermined appropriate density. After 2 days, 100 microliters of purified antibody was diluted into media, and then were transferred to the cell plates and incubated in a 5% $CO_2$ incubator for 5 days. The plate was then emptied by inverting and blotted dry. Room temperature DPBS containing $MgCl_2$ and $CaCl_2$ was dispensed into each well from a multichannel squeeze bottle, tapped three times,

TABLE 1

| Clone | Isotype ELISA Fold (above bkgd) | | Cytotoxicity (%) | | | | | | Binding (above bkgd) | | |
|---|---|---|---|---|---|---|---|---|---|---|---|
| | | | HT-29 | | SW1116 | | SW620 | | HT-29 | SW1116 | SW620 |
| | IgG | IgM | Average | CV | Average | CV | Average | CV | Fold | Fold | Fold |
| 10A304.7 | 39.0 | 0.7 | −57 | 6 | 11 | 13 | −23 | 1 | 22.8 | 13.1 | 23.9 |
| 3BD-27 | | | −34 | 5 | −26 | 12 | 76 | 49 | | | |
| $NaN_3$ | | | 61 | 10 | | | 68 | 16 | | | |
| Cycloheximide | | | 23 | 8 | 17 | 14 | −2 | 8 | | | |
| Anti-EGFR (C225) | | | | | 13 | 10 | | | | | | antibody to HT-29 and SW620 cancer cells by the cell ELISA assay, this did not induce cytotoxicity. This suggested that antibody binding alone was not sufficient to mediate cytotoxicity of 10A304.7 against HT-29 and SW620 cells. As tabulated in Table 1, the 3BD-27 antibody, of the same isotype as the 10A304.7 antibody and previously known not to bind to HT-29 colon cancer cells, did not produce cytotoxicity in that cancer cell line. The known non-specific cytotoxic agents sodium azide and cycloheximide produced cytotoxicity as expected. By way of comparison, the well-defined anti-cancer antibody C225 produced 13% cytotoxicity in SW1116 cancer cells. Results from Table 1 indicate that binding of 10A304.7 to cancer cells may be an important step in producing cytotoxicity but it is not sufficient by itself in mediating this event.

EXAMPLE 2

Antibody Production

10A304.7 monoclonal antibody was produced by culturing the hybridomas in CL-1000 flasks (BD Biosciences, Oakville, ON) with collections and reseeding occurring twice/week and standard antibody purification procedures with Protein G Sepharose 4 Fast Flow (Amersham Biosciences, Baie d'Urfé, QC). It is within the scope of this invention to utilize monoclonal antibodies which are humanized, chimerized or murine antibodies. 10A304.7 was compared to a number of both positive (anti-Fas (EOS9.1, IgM, kappa, 20 mg/mL, eBioscience, San Diego, Calif.), anti-Her2/neu (IgGi, kappa, 10 mg/mL, Inter Medico, Markham, ON), anti-EGFR (C225, IgG1, kappa, 5 mg/mL, Cedarlane, Homby, ON), Cycloheximide (100 mM, Sigma, Oakville, ON), and $NaN_3$ (0.1%, Sigma, Oakville, ON)) and negative (107.3 (anti-TNP, IgG1, kappa, 20 mg/mL, BD emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel and the results were tabulated in Table 2. The data represented an average of four experiments tested in triplicate and presented qualitatively in the following fashion: 4/4 experiments with 15% cytotoxicity above background (++++), 2/4 experiments with 15% cytotoxicity above background (+++), at least 2/4 experiments with 10–15% cytotoxicity above background (++), and at least 2/4 experiments with 8–10% cytotoxicity above background. Unmarked cells in Table 2 represented inconsistent or effects less than the threshold cytotoxicity. The 10A304.7 antibody produced 35% of the cytotoxic effect of the well-described anti-EGFR antibody C225, which induced 31% cytotoxicity in the SW1116 colon cell line. The effect of both antibodies on this cell line is consistent with results in Table 1. Further, 10A304.7 induced significantly higher cytotoxicity against other cancer cells, compared with C225, including the breast cancer cell lines MDA MB 231 (111%) and MCF-7 (850%), the prostate cancer cell line PC-3 (375%), and the ovarian cancer cell line OVCAR (667%). Importantly, 10A304.7 did not produce cytotoxicity against a number of non-cancer cells such as CCD 27sk or Hs888 Lu, indicating that the antibody has specificity towards various cancer cells. The chemical cytotoxic agents induced their expected cytotoxicity while a number of other antibodies which were included for comparison also performed as expected given the limitations of biological cell assays.

TABLE 2

| | Colon | | | | | | Pancreas | Breast | | Prostate | Ovary |
|---|---|---|---|---|---|---|---|---|---|---|---|
| | Caco-2 | DLD-1 | Lovo | HT-29 | SW1116 | SW820 | BxPC-3 | MB-231 | MCF-7 | PC-3 | OVCAR |
| 10A304.7 (20 μg/mL) | | | | ++ | | | | ++ | ++++ | +++ | ++++ |
| Positive Controls | | | | | | | | | | | |
| Anti-Fas (20 μg/mL) | | ++ | ++++ | | | | ++++ | | | ++ | ++++ |
| Anti-Her2/neu (10 μg/mL) | | | | | | | | | | | |
| Anti-EGFR (c225, 5 μg/mL) | +++ | ++++ | | | ++++ | | | + | | | |
| Cycloheximide (100 μM) | ++++ | ++++ | ++++ | ++++ | ++++ | ++++ | ++++ | ++++ | ++++ | ++++ | ++++ |
| Negative Controls | | | | | | | | | | | |
| IgG1 (107.3, 20 μg/mL) | | + | | | | | | + | + | | |
| IgG2b (MPC-11, 20 μg/mL) | | + | | | | | | | | | |
| IgG Buffer (2%) | | | | | | | | | | | |

Cells were prepared for FACS by initially washing the cell monolayer with DPBS (without $Ca^{++}$ and $Mg^{++}$). Cell dissociation buffer (INVITROGEN) was then used to dislodge the cells from their cell culture plates at 37° C. After centrifugation and collection the cells were resuspended in Dulbecco's phosphate buffered saline containing $MgCl_2$, $CaCl_2$ and 25% fetal bovine serum at 4° C. (wash media) and counted, aliquoted to appropriate cell density, spun down to pellet the cells and resuspended in staining media (DPBS containing $MgCl_2$, $CaCl_2$ and 2% fetal bovine serum) at 4° C. in the presence of test antibodies (10A304.7) or control antibodies (isotype control, anti-EGF-R, or anti-Fas) at 20 micrograms/mL on ice for 30 minutes. Prior to the addition of Alexa Fluor 488-conjugated secondary antibody the cells were washed once with wash media. The Alexa Fluor 488-conjugated antibody in staining media was then added for 20 minutes. The cells were then washed for the final time and resuspended in staining media containing 1 microgram/mL propidium iodide. Flow cytometric acquisition of the cells was assessed by running samples on a FACScan using the CellQuest software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform speak with a median fluorescent intensity of approximately 1–5 units. Live cells were acquired by gating for FSC and propidium iodide exclusion. For each sample, approximately 10,000 live cells were acquired for analysis and the results presented in Table 3.

Table 3 tabulated the mean fluorescence intensity fold increase above isotype control and is presented qualitatively as: less than 3 to 5 (+); 5 to 25 (++); 25 to 50 (+++); and above 50 (++++). Representative histograms of 10A304.7 antibodies were compiled for FIG. 1 and evidence of the binding characteristics, inclusive of illustrated bimodal peaks in some cases. 10A304.7 non-specifically bound to all cell lines, including high binding to the non-cancer cells CCD-27sk and Hs888.Lu, but the degree of binding differed between the various cell lines. 10A304.7 thus selectively bound to the cell lines at different levels. Results from Tables 2 and 3 indicate that the binding of 10A304.7 to tumor cells is necessary for antibody-mediated cytotoxicity but it is not sufficient in triggering this event.

TABLE 3

| | Colon | | | | | | Pancreas | Breast | | Prostate | Ovary | Normal Cells | |
|---|---|---|---|---|---|---|---|---|---|---|---|---|---|
| Antibody | CaCo-2 | DLD-1 | Lovo | HT-29 | SW1116 | SW620 | BxPC-3 | MB-231 | MCF-7 | PC-3 | OVCAR | COD27sk | Hs888Lu |
| 10A304.7 (20 μg/mL) | (bimodal) ++++ | ++ | +++ | ++++ | +++ | ++++ | +++ | ++++ | ++ | (bimodal) ++++ | ++++ | ++++ | ++++ |
| Anti-Fas (20 μg/mL) | | ++ | ++ | ++ | + | | ++ | | | | ++ | ++ | +++ |
| Anti-EGFR (c225, 5 μg/mL) | ++ | | ++ | +++ | (bimodal) ++ | | +++ | ++++ | ++ | (bimodal) +++ | +++ | ++ | +++ |

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated monoclonal antibody encoded by the clone deposited with the ATCC as Accession Number PTA-5065.

2. The antibody of claim 1, which is a humanized antibody.

3. The antibody of claim 1, which is a chimerized antibody.

4. Antigen binding fragments of the isolated monoclonal antibody of claim 1.

5. Antigen binding fragments of the humanized antibody of claim 2.

6. Antigen binding fragments of the chimerized antibody of claim 3.

7. The isolated antibody or antigen binding fragments of any one of claims 1, 2, 3, 4, 5 or 6 conjugated with a member selected from the group consisting of cytotoxic moieties, enzymes, radioactive compounds, and hematogenous cells.

8. The isolated clone deposited with the ATCC as Accession Number PTA-5065.

9. A method for inducing cellular cytoxity of cancerous cells in a tissue sample selected from a human tumor comprising:

providing a tissue sample from said human tumor;

providing an isolated monoclonal antibody encoded by the clone deposited with the ATCC as Accession Number PTA-5065 or an antigen binding fragment thereof;

contacting said isolated monoclonal antibody or antigen binding fragment thereof with said tissue sample.

10. The binding assay of claim 9 wherein the tissue sample is obtained from a human tumor originating in a tissue selected from the group consisting of colon, ovarian, lung, and breast tissue.

* * * * *